(12) United States Patent
Friedman

(10) Patent No.: US 8,388,603 B1
(45) Date of Patent: Mar. 5, 2013

(54) DEVICE FOR DETRACTION OF FLUID FROM FLOW LINE FOR TEMPORARY STORAGE AND LATER USE

(75) Inventor: Steven Friedman, San Francisco, CA (US)

(73) Assignee: Steven Friedman, San Francisco, CA (US)

(*) Notice: Subject to any disclaimer, the term of this patent is extended or adjusted under 35 U.S.C. 154(b) by 295 days.

(21) Appl. No.: 12/723,905

(22) Filed: Mar. 15, 2010

Related U.S. Application Data

(60) Provisional application No. 61/210,383, filed on Mar. 19, 2009.

(51) Int. Cl.
*A61M 25/16* (2006.01)
*A61M 25/18* (2006.01)

(52) U.S. Cl. ............................. 604/535; 604/537

(58) Field of Classification Search .......... 604/533–284
See application file for complete search history.

(56) References Cited

U.S. PATENT DOCUMENTS 6,468,261 B1 * 10/2002 Small et al. ................... 604/535

* cited by examiner

*Primary Examiner* — Kevin C Sirmons
*Assistant Examiner* — Bradley Osinski

(57) ABSTRACT

A device detracts fluid from a flow line into a repository for temporary storage and later use. Before an infusion set is changed, medication from the infusion set is detracted into the repository, where it is temporarily stored. Once the new infusion set is connected, medication is dispensed from the repository into the flow line of the new infusion set. The device thus reduces or eliminates waste of medication that was in the flow line of the infusion set, by saving the medication in the repository while the infusion set is being changed.

25 Claims, 13 Drawing Sheets

DEVICE FOR DETRACTION OF FLUID FROM FLOW LINE FOR TEMPORARY STORAGE AND LATER USE

CROSS-REFERENCE TO RELATED APPLICATIONS

This application claims priority from U.S. Provisional Application No. 61/210,383, for "Rewind. A medication device designed to detract fluid from a flow line, and then dispense the fluid back when the flow line is replaced [sic]," filed on Mar. 19, 2009, which is incorporated herein by reference.

This application is related to U.S. Utility application Ser. No. 12/246,230, for "Medication Delivery Device," filed on Oct. 6, 2008, which is incorporated herein by reference.

BACKGROUND OF THE INVENTION

1. Field of the Invention

The present invention relates to a medication delivery device and method of using same, and more particularly, to a device and method for detracting fluid from a flow line into a repository for temporary storage and later use.

2. Description of the Related Art

Many individuals suffer from chronic conditions that require them to self-administer medication via injection, either at regular intervals to manage chronic conditions such as diabetes, or in response to certain emergency conditions.

To be effective, an injection device delivers medication to subcutaneous tissue located below the skin. For management of chronic conditions requiring periodic medication, a source of medication, such as a pump, may operate in connection with an infusion set that provides constant access to the patient's subcutaneous tissue. The infusion set consists of two parts: an infusion site including a plastic housing that contains a subcutaneous needle, and a tubing and connector assembly. The injection device can be attached to the tubing and connector assembly when medication is to be administered.

A pump is an example of a medication delivery device that allows self-administration of medication according to well known techniques for diabetes patients and other patients with chronic conditions. FIG. 1 illustrates an example of a pump 102 according to the prior art, shown connected to a flow line 104 which can pass medication to an infusion site. In operation, pump 102 can remain tethered to the infusion site, via flow line 104, to deliver a gradual flow of medication.

FIG. 2 illustrates an example of an infusion set 200 that can be used in connection with a pump 102 for self-administration of medication according to the prior art, for example for intensive insulin therapy. Infusion set 200 includes flow line 104, which may be constructed from plastic or rubber tubing, adhesive mount 202 for connection to the patient, and subcutaneous cannula (not shown) housed in the adhesive mount, for delivering medication to the patient. Flow line 104 is connected to pump 102 via pump connector 201 and is connected to adhesive mount 202 via site connector 203.

In general, infusion sets 200 must be replaced periodically, such as every two to three days, in order to prevent infection. When an infusion set 200 is discarded, any medication in flow line 104 is wasted. What is needed is a mechanism for reducing or eliminating waste by avoiding or limiting the need to discard medication when changing an infusion set 200. What is further needed is waste reduction device that is easy to use and that does not contaminate the medication.

SUMMARY OF THE INVENTION

The present invention is a device for detracting fluid from a flow line 104 into a repository, or chamber, for temporary storage and later use. Before an infusion set 200 is changed, medication from the infusion set 200 is detracted into a resizable chamber, where it is temporarily stored. Then, once the new infusion set 200 is connected, medication is dispensed from the chamber into the flow line 104 of the new infusion set 200. In this manner, the device of the present invention reduces or eliminates waste of medication that was in the flow line 104 of the infusion set 200, by saving the medication in the repository while the infusion set 200 is being changed.

In one embodiment, the repository is implemented as part of an assembly located between infusion set 200 and pump 102; for example, it may be attached to or part of pump connector 201. In another embodiment, the repository assembly is part of the overall pump assembly, and is included within the housing that contains the pump. Manipulable components within the repository assembly control the flow of fluid from flow line 104 to the resizable chamber and from the resizable chamber back to flow line 104. In one embodiment, flow between pump 102 and the repository assembly can be blocked when needed, to avoid unwanted flow of medication from pump 102 into the chamber.

BRIEF DESCRIPTION OF THE DRAWINGS

The accompanying drawings illustrate several embodiments of the invention and, together with the description, serve to explain the principles of the invention.

DETAILED DESCRIPTION OF THE EMBODIMENTS

The present invention is now described more fully with reference to the accompanying Figures, in which several embodiments of the invention are shown. The present invention may be embodied in many different forms and should not be construed as limited to the embodiments set forth herein.

Rather these embodiments are provided so that this disclosure will be complete and will fully convey the invention to those skilled in the art.

In the following description, the invention is set forth as a repository assembly that is connected between a pump and an infusion set. However, one skilled in the art will recognize that the invention can be implemented in other ways as well. For example, different mechanisms can be used for controlling the flow of fluid between the repository assembly and other components. It will be apparent from the description provided herein that many other variations are possible, and that the particular embodiments set forth herein are intended to be exemplary and not limiting.

Figure 1:
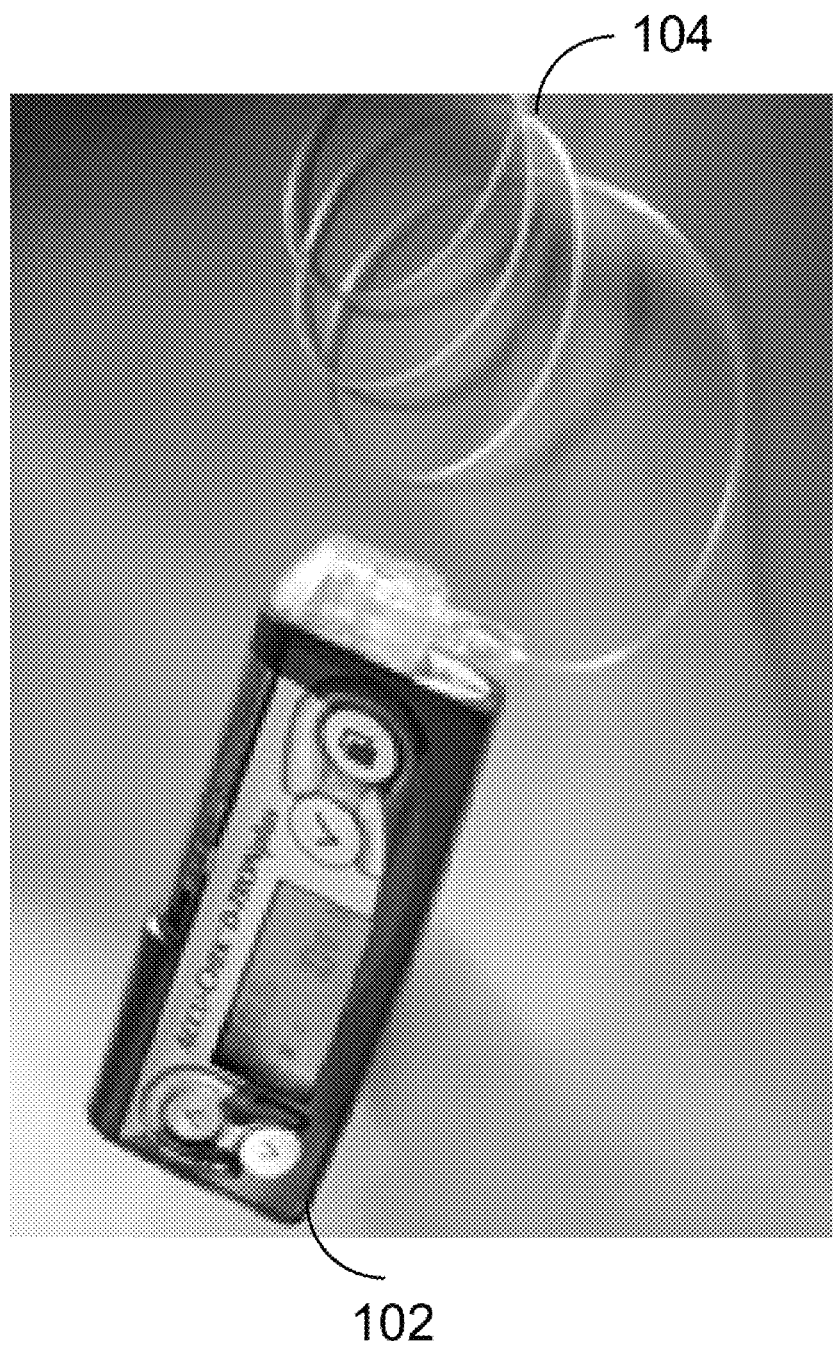
FIG. 1 is a diagram depicting an example of a pump connected to a flow line, according to the prior art.
Figure 2:
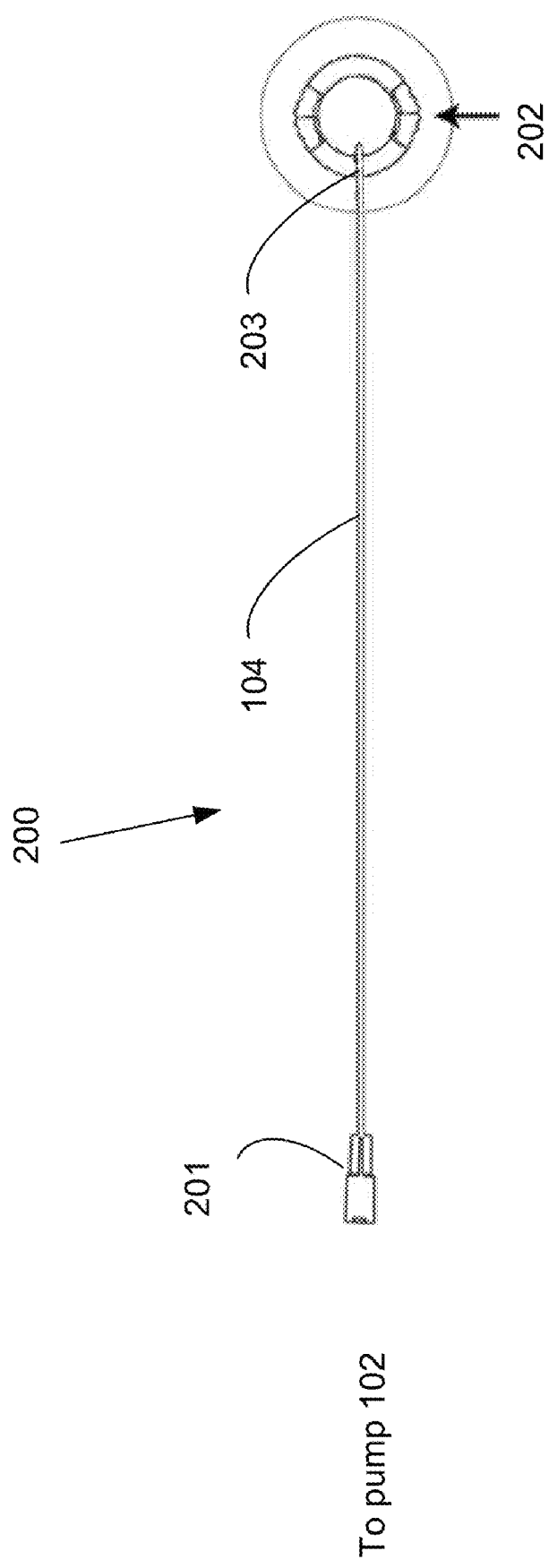
FIG. 2 is a diagram depicting an example of an infusion set, according to the prior art.
Figure 3:
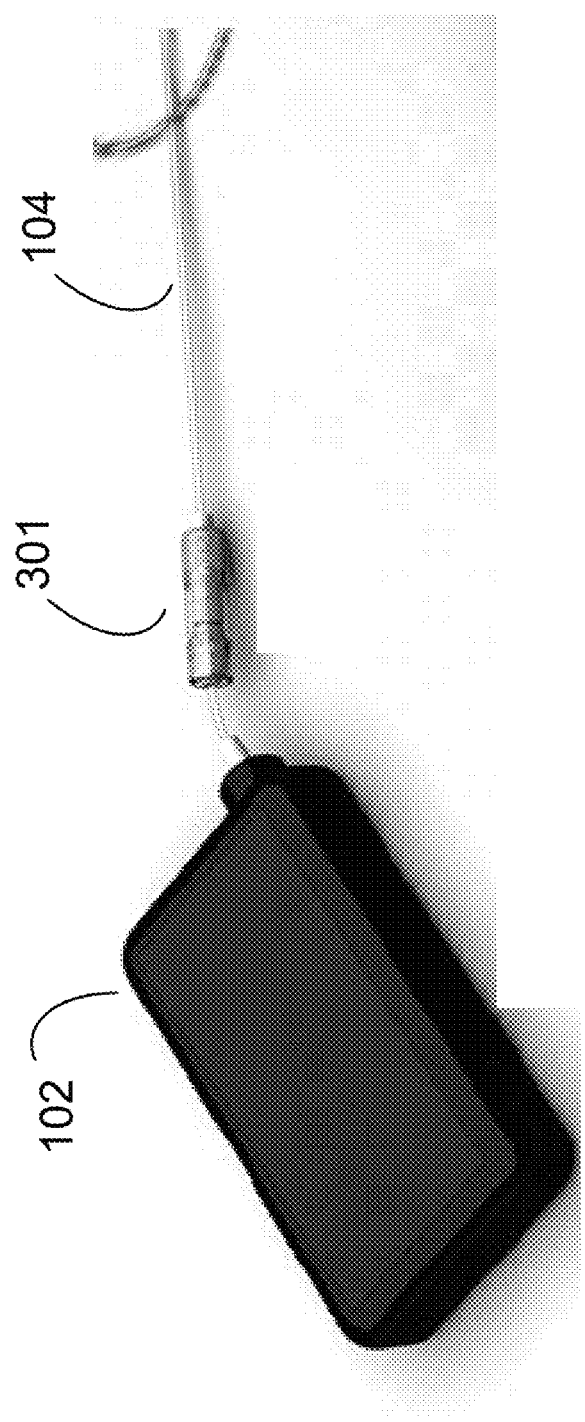
FIG. 3 is a diagram depicting a repository assembly according to one embodiment, connected between a pump and a flow line of an infusion set.
Figure 4:
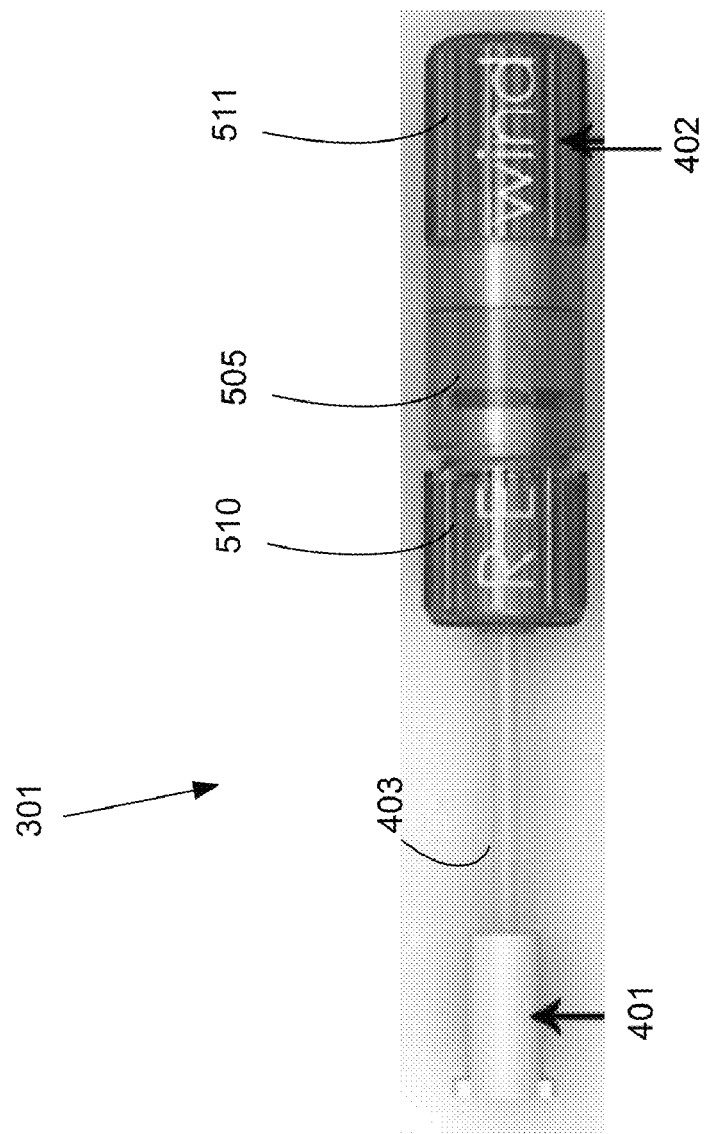
FIG. 4 is a diagram depicting a repository assembly according to one embodiment.

Referring now to FIG. 3, there is shown a diagram depicting a repository assembly 301 according to one embodiment, connected as an intermediary device between a pump 102 and a flow line 104 of an infusion set 200. Referring now also to FIG. 4, there is shown a diagram depicting repository assembly 301 according to one embodiment. In one embodiment, repository assembly 301 includes a main body 505 and movable connector components 510, 511 whose operation will be described in more detail below. In one embodiment, repository assembly 301 also includes a pump connector 401 for attaching to pump 102, and tubing 403 to connect pump connector 401 to main body 505 via component 510. A portion of component 511 is an infusion set connector 402 for attaching to flow line 104 of infusion set 200. In one embodiment, pump connector 401 is a male luer connector for engagement with a female luer connector of pump 101, while infusion set connector 402 is a female luer connector for engagement with a male luer connector of flow line 104. One skilled in the art will recognize that any type of connector can be used between the various components depicted in FIGS. 3 and 4. In one embodiment, as described in more detail below, tubing 403 can be omitted, and component 510 can be directly connected to pump 102.

In operation, prior to disconnection of infusion set 200, repository assembly 301 detracts fluid from flow line 104, temporarily storing the fluid in a chamber formed between main body 505 and connector component 511. This allows infusion set 200 to be replaced without wasting medication (or while minimizing waste of medication). Once a new infusion set 200 has been connected, repository assembly 301 dispenses the stored fluid into new flow line 104. Various components of repository assembly 301 are manipulable, as described below, so as to provide the user with the ability to control flow of fluid into and out of repository assembly 301 in the course of operating the device. One skilled in the art will recognize that the particular appearance and operation of repository assembly 301 depicted herein is merely exemplary, and that other configurations and methods of operation can be implemented without departing from the essential characteristics of the invention as claimed herein.

Figure 5:
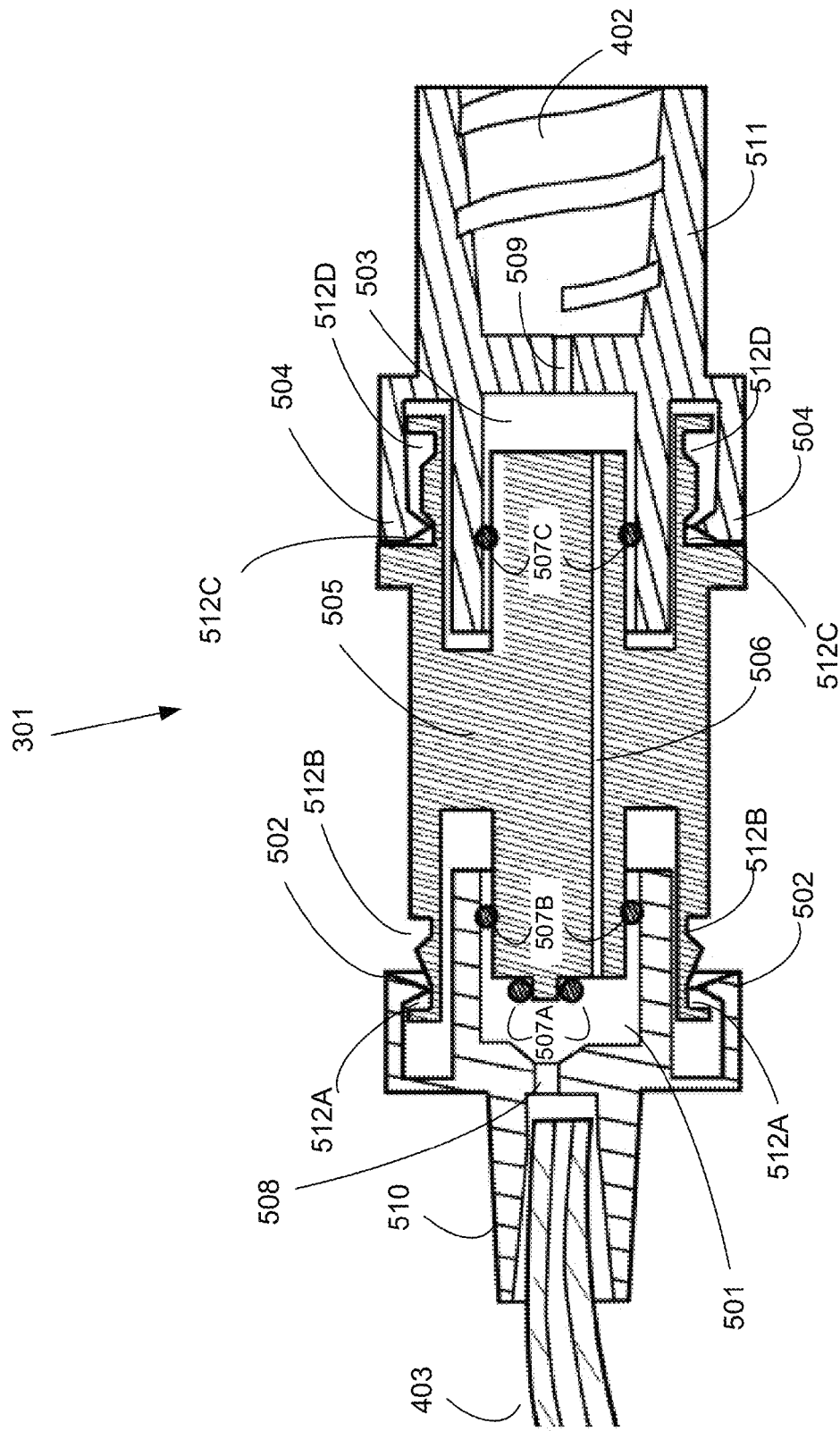
FIG. 5 is a cross-sectional diagram depicting a repository assembly according to one embodiment.

Referring now to FIG. 5, there is shown a cross-sectional diagram depicting repository assembly 301 according to one embodiment. In the embodiment, repository assembly 301 includes connector components 510, 511 that are movable with respect to main body 505. Connector components 510, 511 and main body 505 can be constructed from any suitable material, such as polycarbonate (PC) and/or polyethylene (PE) plastics, metal, rubber, or the like. In one embodiment, appropriate seals are formed among the various components so as to prevent or minimize leakage of fluid while still enabling movement of the components with respect to one another. In one embodiment, repository assembly 301 is approximately 35 mm in length, and has a diameter of approximately 10 mm. One skilled in the art will recognize that the device of the present invention can be constructed using other materials and having other dimensions.

In operation, repository assembly 301 is positioned between pump 102 and flow line 104 of infusion set 200. Connector component 510 is adapted to be coupled to tubing 403, which carries fluid from pump 102. In one embodiment, connector component 510 is affixed to tubing 403 using an adhesive or some other mechanism. Connector component 511 is adapted to be coupled to flow line 104 of infusion set 200, for example by being shaped to form female infusion set connector 402. As shown in FIG. 5, female infusion set connector 402 can be threaded to improve the quality and stability of the engagement with flow line 104.

In one embodiment, connector components 510, 511 are adapted to be movable with respect to main body 505. For example, in the embodiment shown in FIG. 5, connector components 510, 511 include hooks 502, 504 that variously engage with detents 512A-D in main body 505 to move the components with respect to one another and to hold connector components 510, 511 in various positions with respect to main body 505. The operation and function of connector components 510, 511 in various positions will be described in more detail below.

In one embodiment, a space between connector component 510 and main body 505 forms chamber 501, while a space between connector component 511 and main body 505 forms chamber 503. Chambers 501, 503 change in size in response to the movement of connector components 510, 511, as described in more detail below. Opening 508 in connector component 510 permits fluid to flow from tubing 403 to chamber 501. Opening 506 in main body 505 permits fluid to flow from chamber 501 to chamber 503. Opening 509 in connector component 511 permits fluid to flow between chamber 503 and flow line 104 of infusion set 200. Specifics as to timing and direction of fluid flow will be described in more detail below.

In one embodiment, O-rings, gaskets, or other sealing mechanisms can be included so as to ensure proper fluid flow within and among chambers 501, 503 and to minimize or eliminate leakage while still permitting movement of components 510, 511 with respect to main body 505. In FIG. 5, cross-sections of O-rings 507A-C are depicted as selectively forming seals between main body 505 and respective connector components 510, 511.

Figure 6A:
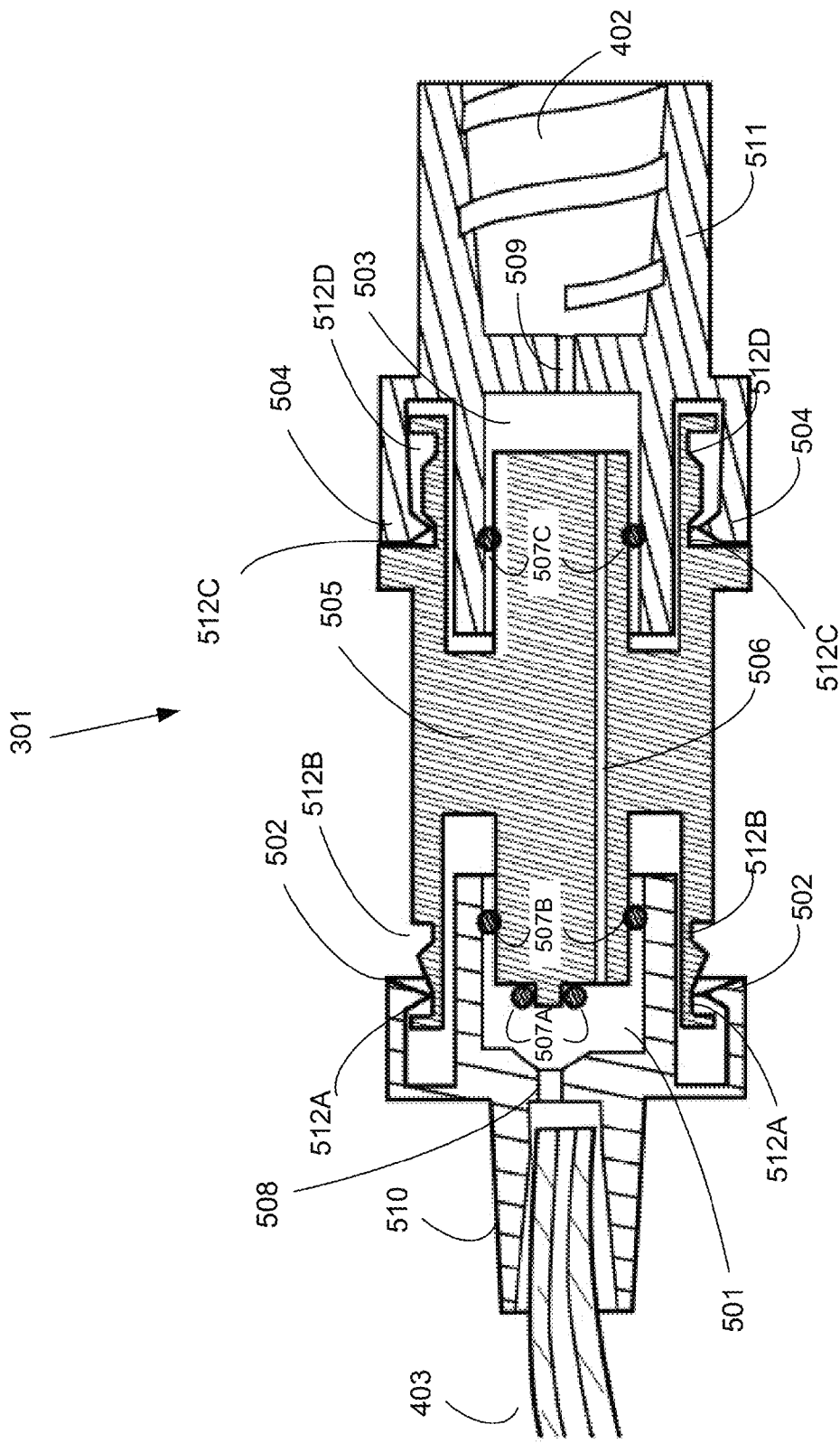
FIGS. 6A through 6C are cross-sectional diagrams depicting operation of a repository assembly to detract medication from a flow line, according to one embodiment.
Figure 6B:
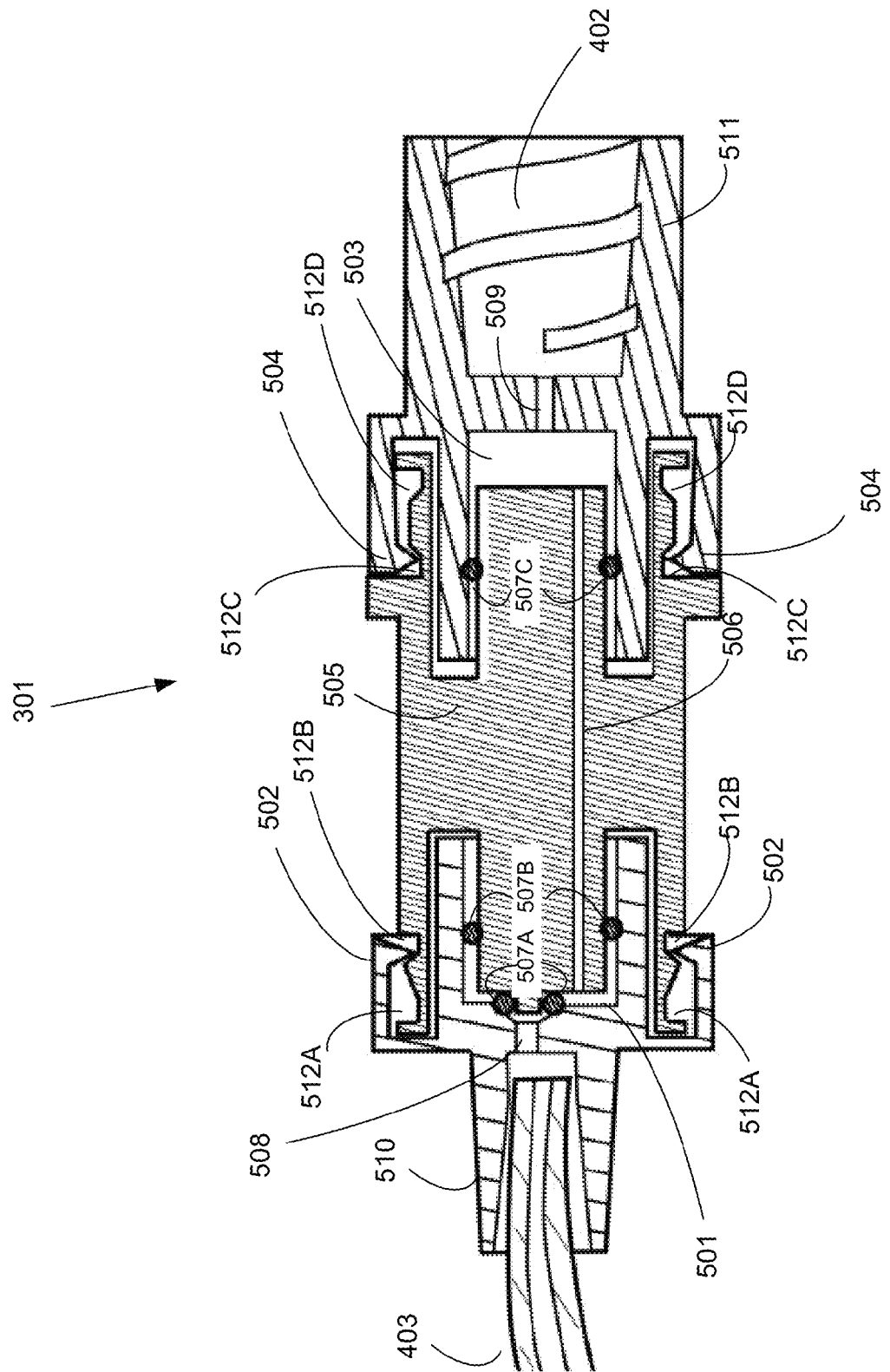
Figure 6C:
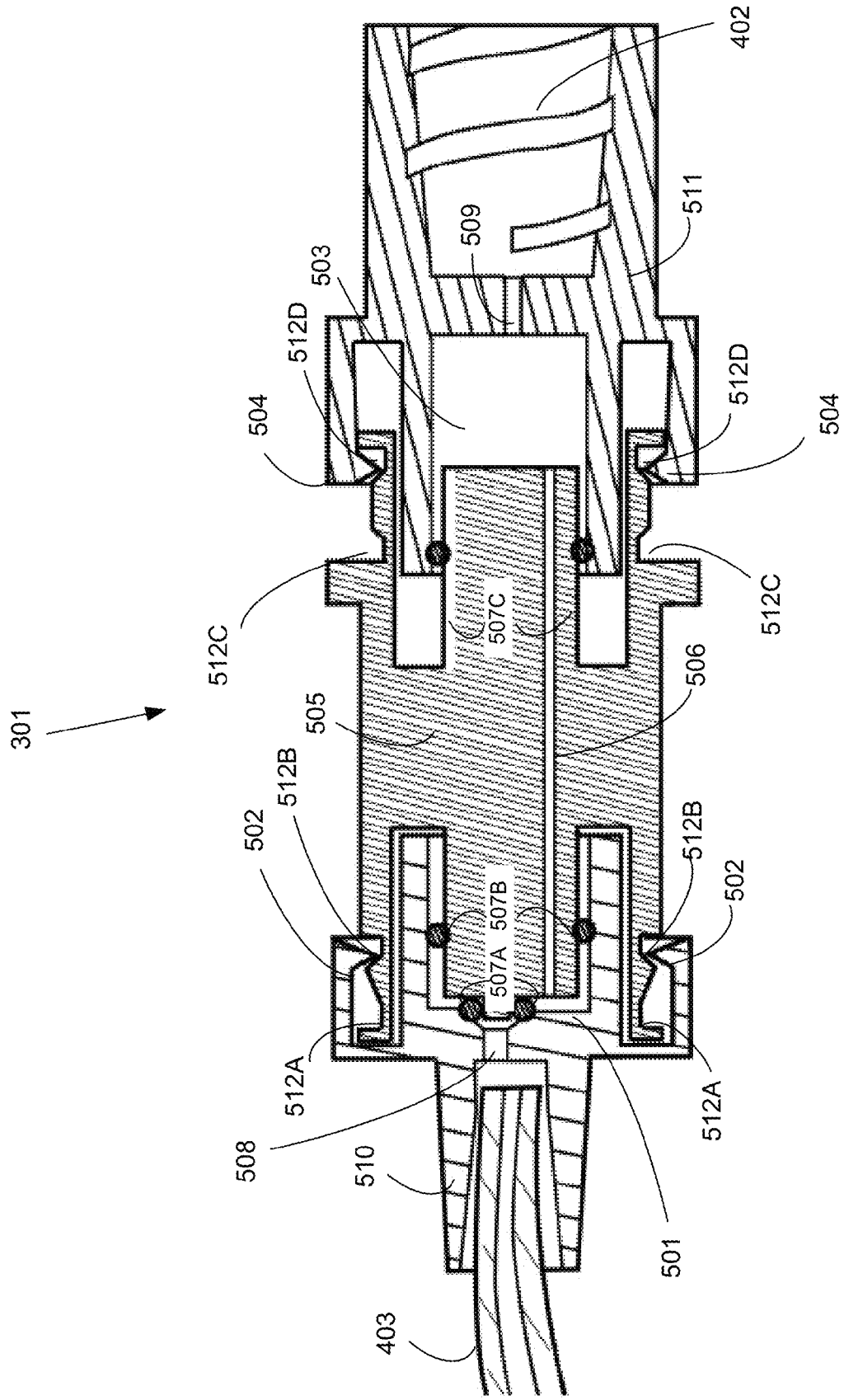

Referring now to FIGS. 6A through 6C, there is shown a series of cross-sectional diagrams depicting operation of the repository assembly of the present invention to detract medication from a flow line, according to one embodiment.

Figure 7:
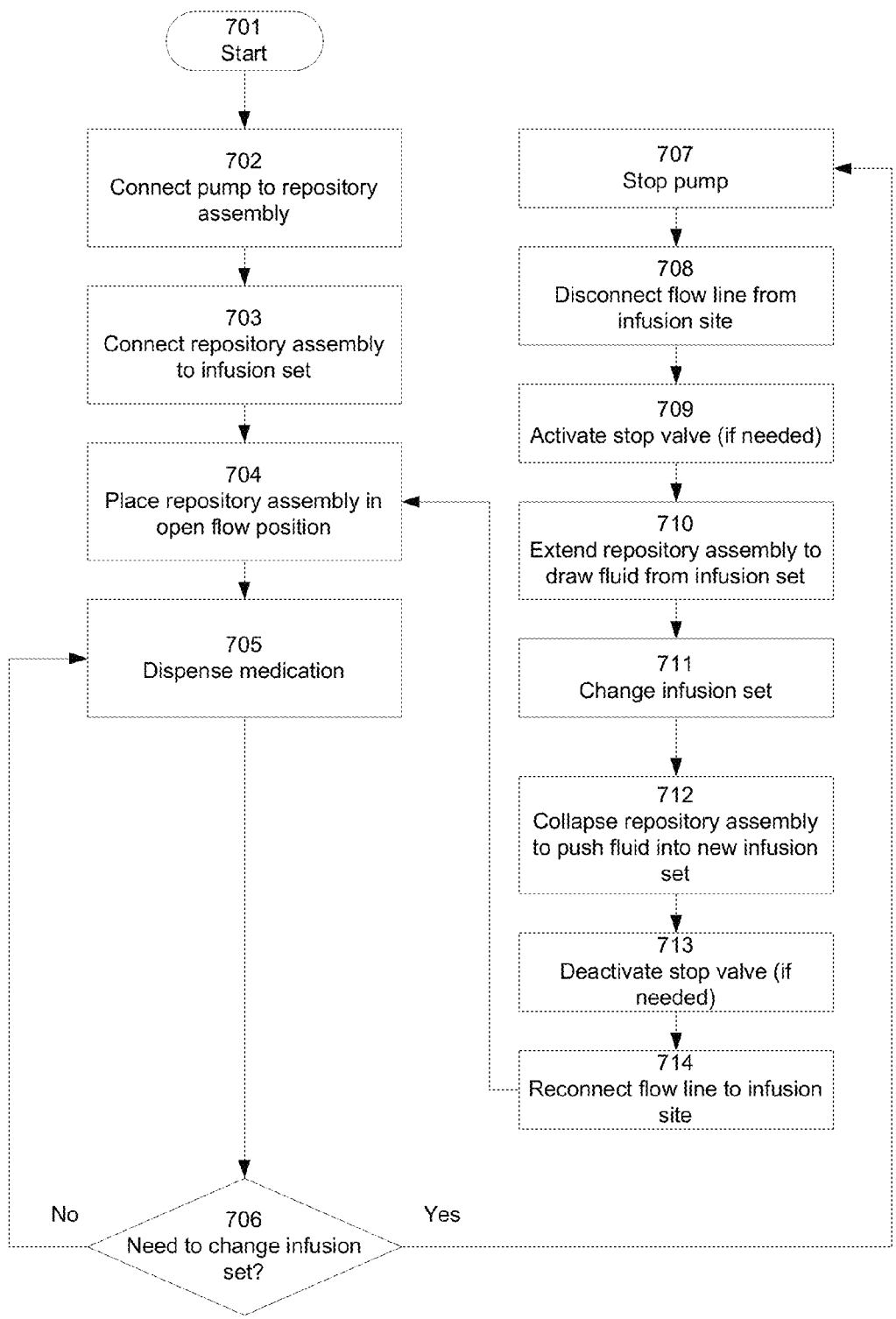
FIG. 7 is a flow diagram depicting a method of detracting medication from a flow line into a repository while an infusion set is changed, according to one embodiment.

Referring now also to FIG. 7, there is shown diagram depicting a method of detracting medication from a flow line into a repository while an infusion set is changed, according to one embodiment.

Initially, the patient (or doctor) connects 702 pump 102 to repository assembly 301, and connects 703 repository assembly 301 to infusion set 200. Repository assembly 301 is placed 704 in an open flow position, allowing fluid to pass from pump 102, through repository assembly 301, and into infusion set 200. Medication can then be dispensed 705 to the patient via the infusion set 200.

FIG. 6A depicts repository assembly 301 in an open flow position. Hooks 502 are engaged with detents 512A and hooks 504 are engaged with detents 512C. In this position, fluid (such as medication) passes freely from pump 102 (not shown) through repository assembly 301 and out to flow line 104 (not shown) via infusion set connector 402. Specifically, in the open flow position, fluid has a clear flow path through tubing 403 into chamber 501 via opening 508, then into chamber 503 via opening 506, and finally into flow line 104 via opening 509 and infusion set connector 402. O-ring 507B is seated between component 510 and main body to ensure that fluid does not leak out from chamber 501. O-ring 507C is seated between component 511 and main body to ensure that fluid does not leak out from chamber 503. In this position, O-ring 507A does not perform any function.

When infusion set 200 needs to be changed 706, steps 707 through 714 are performed so as to detract fluid from infusion set 200 into repository assembly 301. In this manner, fluid in flow line 104 of infusion set 200 is not wasted. First, the user stops 707 pump 102 and disconnects 708 flow line 104 from the infusion site. Then, a stop valve is activated 709 (this step is optional, as described below). The purpose of the stop valve is to ensure that: 1) when repository assembly 301 is extended as described below, fluid will be drawn from infusion set 200 and not from pump 102; and 2) when repository assembly 301 is collapsed after infusion set 200 is changed, as described below, fluid will be not be forced back toward pump 102.

FIG. 6B depicts repository assembly 301 in a position wherein a stop valve (implemented as O-ring 507A) has been activated. Here, component 510 has been pushed toward main body 505, so that hooks 502 are now engaged with detents 512B (hooks 504 are still engaged with detents 512C). In this position, O-ring 507A is compressed between component 510 and main body 505, and chamber 501 has been reduced in size. The fluid flow path from tubing 403 into chamber 501 is now blocked, ensuring that no fluid can pass from pump 102 into repository assembly 301 when repository assembly 301 is extended as described below. This position thus ensures that fluid will be detracted from infusion set 200 rather than from pump 102.

The stop valve and step 709 are optional. As described above, the purpose of the stop valve is to ensure that, when repository assembly 301 is extended 710, fluid is drawn from infusion set 200 and not from pump 102. In an embodiment where pump 102 can be shut off or otherwise configured so that no fluid can pass into repository assembly 301 via tubing 403, there may be no need for a stop valve. For example, if pump 102 (or other medication source) includes a plunger valve with sufficient friction or some other mechanism to prevent unwanted fluid flow into repository assembly, then the stop valve can be omitted, and step 709 can be skipped, since there is no need for the stop valve to prevent fluid from being drawn from pump 102 rather than from infusion set 200. In such an embodiment, O-ring 507A can be omitted, and there need not be any mechanism for blocking flow path at opening 508. As described in more detail below, alternative stop valves can be used.

In step 710, the patient extends repository assembly 301, causing fluid to be drawn from infusion set 200 into chamber 503. FIG. 6C depicts repository assembly 301 in the extended position. Component 511 has been pulled away from main body 505, so that hooks 504 are now engaged with detents 512D (hooks 502 are still engaged with detents 512B). This causes chamber 503 to enlarge in size; the new interior volume creates suction which draws fluid from infusion set 200. Fluid flow from tubing 403 is blocked, so that no fluid enters chamber 503 from pump 102.

In one embodiment, all the fluid in flow line 104 of infusion set 200 is detracted into chamber 503. In another embodiment, some portion of the fluid in flow line 104 of infusion set 200 is detracted into chamber 503, depending on the total amount of fluid present in flow line 104 and on the capacity of chamber 503.

Once fluid has been detracted into chamber 503, the patient changes 711 infusion set 200 by disconnecting it from repository assembly 301 and reconnecting a new infusion set 200. Repository assembly 301 is then collapsed 712 to push the detracted fluid into the new infusion set 200; this step includes, for example, engaging hooks 504 with detents 512C to cause chamber 503 to become smaller and thereby push fluid into new infusion set 200.

The user then deactivates 713 the stop valve (if it was previously activated), and reconnects 714 flow line 104 to the infusion site. If desired, the user can run pump 102 for some short period of time before reconnecting flow line 104, so as to ensure that flow line 104 contains fluid before it is reconnected 714. The method then returns to step 704, wherein repository assembly 301 is placed in the open flow position as depicted in FIG. 6A; this step includes, for example, engaging hooks 502 with detents 512A to reestablish the flow of fluid from pump 102 to infusion set 200, via repository assembly 301.

In one embodiment, component 510 moves approximately 1 mm with respect to main body 505 when engaging or disengaging the stop valve, and component 511 moves approximately 5 mm with respect to main body 505 when extending and/or collapsing assembly 301 to detract and/or dispense fluid. One skilled in the art will recognize that these amounts of movement are merely exemplary, and that the present invention can be implemented using other amounts of movement among components.

One skilled in the art will recognize that the particular arrangement and configuration of repository assembly 301 shown in the Figures and described herein are merely exemplary. Other configurations and arrangements can be implemented without departing from the essential characteristics of the present invention.

Figure 8:
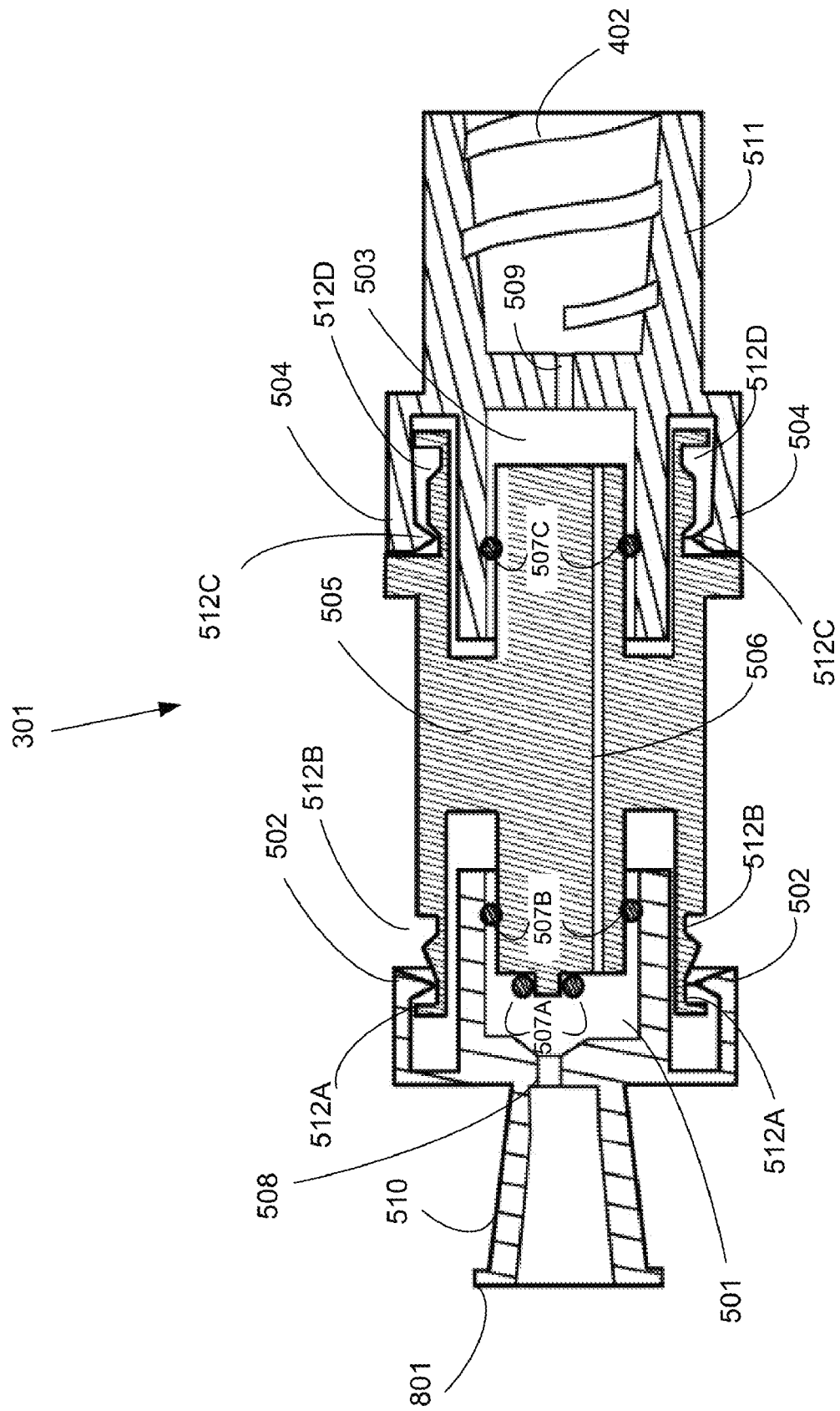
FIG. 8 is a cross-sectional diagram depicting a repository assembly according to another embodiment, wherein the repository connects directly to a pump.

For example, referring now to FIG. 8, there is shown a cross-sectional diagram depicting a repository assembly 301 according to another embodiment, wherein the repository connects directly to pump 102, without any need for tubing 403 or pump connector 401. Here, component 510 engages directly with pump 102, for example via a luer connection. Component 510 is shaped to engage with pump 102, and includes lip 801 to hold it in place. In other respects, the embodiment shown in FIG. 8 is substantially identical to that depicted and described above in connection with FIG. 5, and the operation of the embodiment of FIG. 8 is substantially identical to that described above in connection with FIGS. 6A-6C and 7.

The use of O-ring 507A to implement a stop valve as shown in FIGS. 6B and 6C is merely an example of one embodiment. Other types of stop valves can be used, as will be apparent to one skilled in the art, including for example, mechanisms that operate by moving components with respect to one another in a translational, rotational, or other type of movement.

Figure 9A:
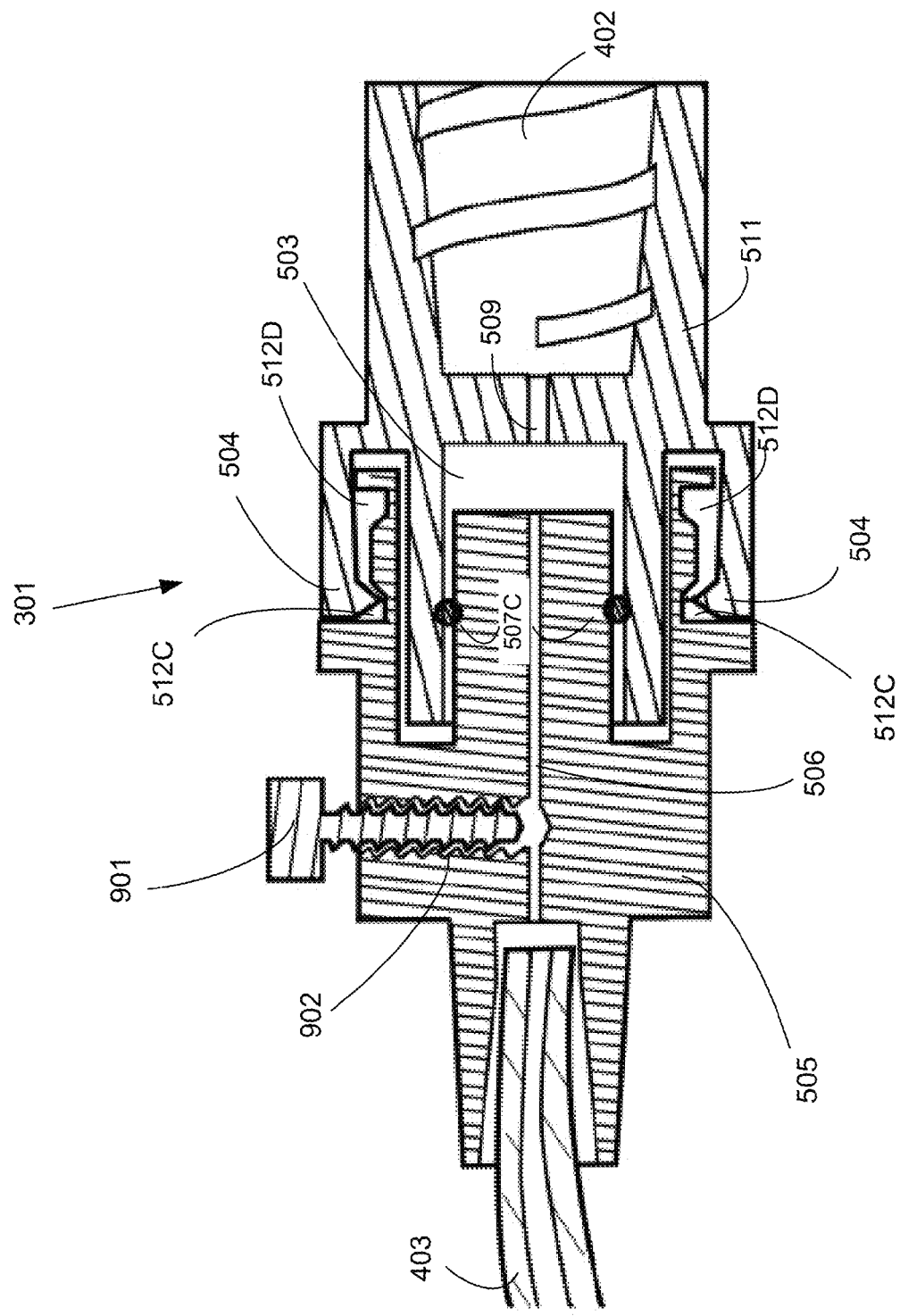
FIGS. 9A through 9C are cross-sectional diagrams depicting operation of an alternative embodiment of a repository assembly to detract medication from a flow line, wherein a stop valve is implemented as a screw.
Figure 9B:
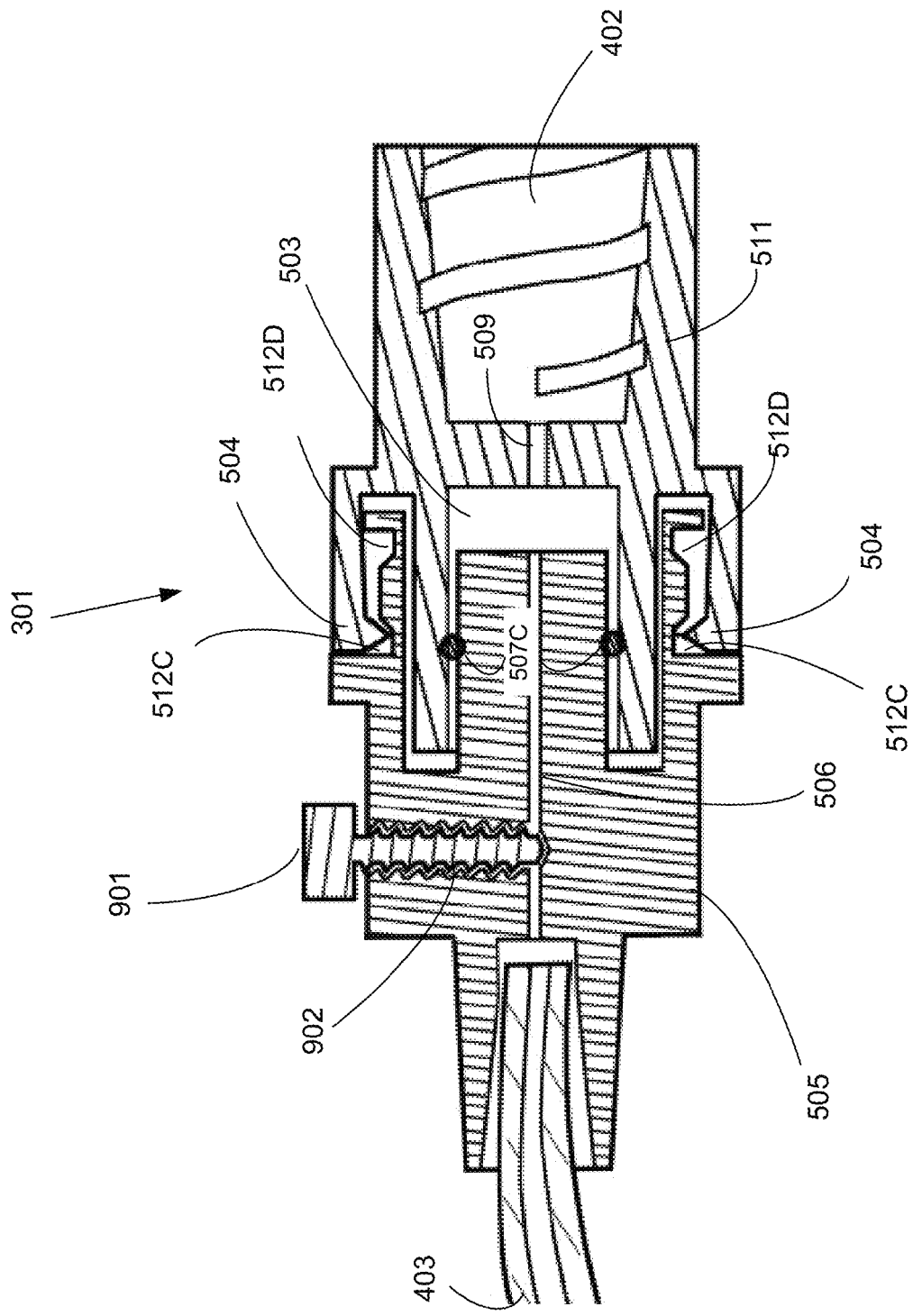
Figure 9C:
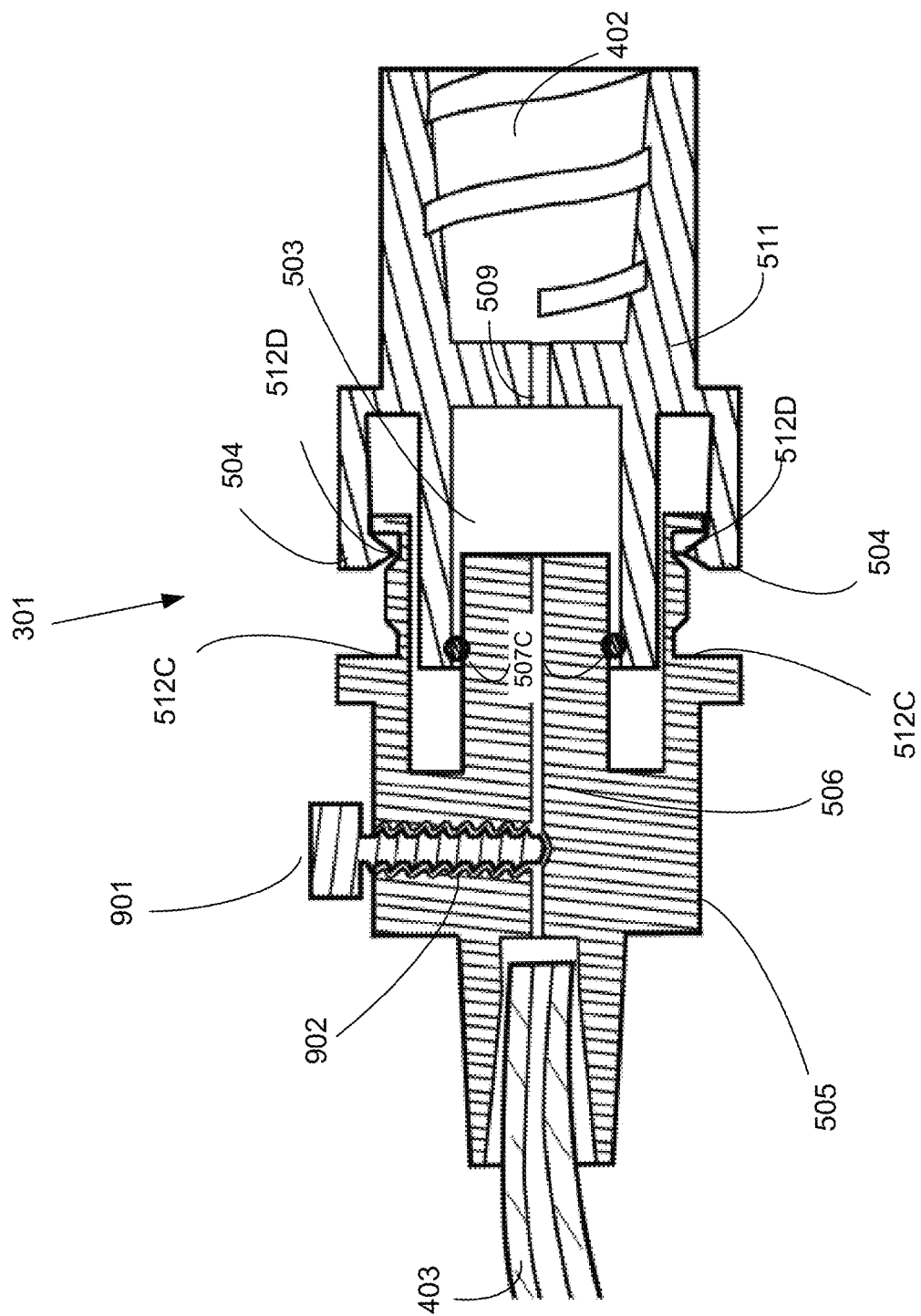

Referring now to FIGS. 9A through 9C, there are shown cross-sectional diagrams depicting operation of an alternative embodiment of repository assembly 301 to detract medication from a flow line, wherein an alternative stop valve mechanism is used.

In the implementation depicted in FIGS. 9A through 9C, component 510 is omitted. Rather, main body 505 is connected directly to tubing 403 (or to pump 102). The stop valve is implemented as a screw 901 that engages with threads 902 in main body 505, so as to selectively block the flow of fluid through opening 506.

FIG. 9A depicts repository assembly 301 in an open flow position, wherein screw 901 is in an open, or loose, position to allow the flow of fluid from tubing 403 into opening 506 and thereby into opening 503 and into infusion set 200 via opening 509 and connector 402.

In order to block flow of fluid from pump 102 into repository assembly 301, the patient turns screw 901 so that it is lowered into the position shown in FIG. 9B. Here, screw 901 blocks the flow of fluid from tubing 403 into opening 506. Thus, screw 901 performs a function analogous to that performed by O-ring 507B when compressed against element 510 as described above in connection with FIG. 6B.

As shown in FIG. 9C, the patient extends repository assembly 301, causing fluid to be drawn from infusion set 200 into chamber 503. In this manner, component 511 is pulled away from main body 505, so that hooks 504 are now engaged with detents 512D. As described above, this causes chamber 503 to enlarge in size; the new interior volume creates suction which draws fluid from infusion set 200. Fluid flow from tubing 403 is blocked by screw 901, so that no fluid enters chamber 503 from pump 102. Once fluid has been detracted into chamber 503, the patient changes the infusion set 200 by disconnecting it from repository assembly 301 and reconnecting a new infusion set 200. Hooks 504 are then engaged with detents 512C to cause chamber 503 to become smaller and thereby push fluid into new infusion set 200. Screw 901 is then opened, so as to reestablish the flow of fluid from pump 102 to infusion set 200, via repository assembly 301.

In another embodiment, repository assembly 301 can be configured as an internal component of pump 102. In such an embodiment, repository assembly 301 is connected to a pump drive system, with both the pump drive system and repository assembly 301 being situated within a common housing. Alternatively, repository assembly 301 can be located at any point along the fluid delivery path from a pump reservoir (or other fluid source) and infusion set 200. In any such embodiment, repository assembly 301 can be an internal component of pump 102 or of a pump assembly, or can be an external component.

In the above description, for purposes of explanation, numerous specific details are set forth in order to provide a thorough understanding of the invention. It will be apparent, however, to one skilled in the art that the invention can be practiced without these specific details. In other instances, structures and devices are shown in block diagram form in order to avoid obscuring the invention.

Reference in the specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment.

As will be understood by those familiar with the art, the invention may be embodied in other specific forms without departing from the spirit or essential characteristics thereof. For example, the particular architectures depicted above are merely exemplary of one implementation of the present invention. In one embodiment, the device of the present invention can be used for functions other than the dispensing of medication. In one embodiment, the device of the present invention can be integrated with other medication delivery devices such as that described in related U.S. Utility application Ser. No. 12/246,230, for "Medication Delivery Device," filed on Oct. 6, 2008, which is incorporated herein by reference.

The functional elements and method steps described above are provided as illustrative examples of one technique for implementing the invention; one skilled in the art will recognize that many other implementations are possible without departing from the present invention as recited in the claims. Likewise, the particular capitalization or naming of the modules, protocols, features, attributes, or any other aspect is not mandatory or significant, and the mechanisms that implement the invention or its features may have different names or formats. In addition, the present invention may be implemented as a method, process, user interface, computer program product, system, apparatus, or any combination thereof. Accordingly, the disclosure of the present invention is intended to be illustrative, but not limiting, of the scope of the invention, which is set forth in the following claims.

What is claimed is:

1. A device for detraction and temporary storage of fluid from a flow line, comprising:
    a first connector, for engagement with a source of fluid;
    a second connector, for engagement with a flow line for carrying the fluid;
    a resizable chamber, coupled to the first and second connectors, for temporarily holding fluid from the flow line;
    a main body comprising at least four engagement elements and an opening for selectively allowing flow of fluid from the first connector into the resizable chamber;
    a first component comprising at least one engagement element, movable with respect to the main body, but not separable therefrom, and wherein the first connector forms part of the first component:
    a second component comprising at least one engagement element, movable with respect to the main body, but not separable therefrom, and wherein the second connector forms part of the second component:
    wherein:
    the engagement element of the first component engages with a first engagement element on the main body to maintain an open position for the valve;
    the engagement element of the first component engages with a second engagement element on the main body to maintain a closed position for the valve;
    the engagement element of the second component engages with a third engagement element on the main body to hold the device in the first position wherein the chamber has the first size; and
    the engagement element of the second component engages with a fourth engagement element on the main body to hold the device in the second position wherein the chamber has the second size larger than the first size;
    and wherein the device has at least two positions, the positions comprising:
    a first position, wherein the chamber is configured to have a first size, for allowing flow of fluid from the source of fluid into the flow line; and
    a second position, wherein the chamber is configured to have a second size larger than the first size, for causing fluid to be detracted from the flow line into the chamber.

2. The device of claim 1, wherein moving the device from the first position to the second position causes the chamber to enlarge in size, generating a vacuum in the chamber to cause fluid to be detracted from the flow line into the chamber.

3. The device of claim 1, wherein the first connector engages with tubing coupled to a pump.

4. The device of claim 1, wherein the source of fluid comprises a pump.

5. The device of claim 1, further comprising a valve for selectively preventing flow of fluid from the source of fluid to the resizable chamber.

6. The device of claim 5, wherein the valve is adapted to prevent flow of fluid from the source of fluid to the resizable chamber while fluid is being detracted from the flow line into the chamber.

7. The device of claim 5, further comprising:
a main body comprising an opening for selectively allowing flow of fluid from the first connector into the resizable chamber;
a first component, movable with respect to the main body, wherein movement of the first component causes the valve to move between an open and closed position; and
a second component, movable with respect to the main body, wherein movement of the second component causes the resizable chamber to change in size between the first size and the second size;
and wherein the first connector forms part of the first component and the second connector forms part of the second component.

8. The device of claim 7, wherein the resizable chamber is formed by a space between the main body and the second component.

9. The device of claim 8, wherein the valve comprises at least one O-ring disposed to selectively form a seal between the first component and the main body, in response to the first component being moved with respect to the main body.

10. The device of claim 7, wherein:
the first component comprises at least one protrusion;
the second component comprises at least one protrusion; and
the main body comprises at least four detents;
and wherein:
the protrusion of the first component engages with a first detent on the main body to maintain an open position for the valve;
the protrusion of the first component engages with a second detent on the main body to maintain a closed position for the valve;
the protrusion of the second component engages with a third detent on the main body to hold the device in the first position wherein the chamber has the first size; and
the protrusion of the second component engages with a fourth detent on the main body to hold the device in the second position wherein the chamber has the second size larger than the first size.

11. The device of claim 7, wherein:
the first component comprises at least one detent;
the second component comprises at least one detent; and
the main body comprises at least four protrusions;
and wherein:
the detent of the first component engages with a first protrusion on the main body to maintain an open position for the valve;
the detent of the first component engages with a second protrusion on the main body to maintain a closed position for the valve;
the detent of the second component engages with a third protrusion on the main body to hold the device in the first position wherein the chamber has the first size; and
the detent of the second component engages with a fourth protrusion on the main body to hold the device in the second position wherein the chamber has the second size larger than the first size.

12. The device of claim 1, further comprising:
a main body comprising an opening for selectively allowing flow of fluid from the first connector to the resizable chamber;
a movable component, movable with respect to the main body, wherein movement of the movable component causes the resizable chamber to change in size;
and wherein the first connector forms part of the main body and the second connector forms part of the movable component.

13. The device of claim 12, wherein the resizable chamber is formed by a space between the main body and the movable component.

14. The device of claim 12, further comprising a valve for selectively preventing flow of fluid from the source to the resizable chamber.

15. The device of claim 14, wherein the valve comprises a threaded male element for engagement with a threaded female element.

16. The device of claim 14, wherein the valve comprises a threaded screw for engagement with threads in the main body.

17. The device of claim 12, wherein:
the movable component comprises at least one engagement element; and
the main body comprises at least two engagement elements;
and wherein:
the engagement element of the movable component engages with a first engagement element on the main body to hold the device in the first position wherein the chamber has the first size; and
the engagement element of the movable component engages with a second engagement element on the main body to hold the device in the second position wherein the chamber has the second size larger than the first size.

18. The device of claim 12, wherein:
the movable component comprises at least one protrusion; and
the main body comprises at least two detents;
and wherein:
the protrusion of the movable component engages with a first detent on the main body to hold the device in the first position wherein the chamber has the first size; and
the protrusion of the movable component engages with a second detent on the main body to hold the device in the second position wherein the chamber has the second size larger than the first size.

19. The device of claim 1, wherein the fluid comprises medication.

20. The device of claim 19, wherein the second connector is adapted to engage with a flow line of an infusion set, for delivery of medication to the infusion set.

21. The device of claim 1, wherein the chamber is adapted to receive substantially all the fluid present in the flow line of the infusion set.

22. The device of claim 1, wherein the chamber is adapted to receive a portion of the fluid present in the flow line of the infusion set.

23. The device of claim 1, second connector comprises a luer connector.

24. The device of claim 1, wherein the device is situated internally within a housing for a pump assembly.

25. The device of claim 1, wherein the device is situated within a housing, and wherein the source of fluid comprises a pump situated within the same housing.

* * * * *